(12) United States Patent
Garnavi et al.

(10) Patent No.: US 10,307,050 B2
(45) Date of Patent: Jun. 4, 2019

(54) EARLY PREDICTION OF HYPERTENSIVE RETINOPATHY

(71) Applicant: International Business Machines Corporation, Armonk, NY (US)

(72) Inventors: Rahil Garnavi, Melbourne (AU); Kerry J. Halupka, Melbourne (AU); Stephen M. Moore, Melbourne (AU); Pallab Roy, Melbourne (AU); Suman Sedai, Melbourne (AU)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/485,023

(22) Filed: Apr. 11, 2017

(65) Prior Publication Data

US 2018/0289252 A1    Oct. 11, 2018

(51) Int. Cl.
*A61B 3/00*    (2006.01)
*A61B 3/12*    (2006.01)
*A61B 3/14*    (2006.01)

(52) U.S. Cl.
CPC .......... *A61B 3/0025* (2013.01); *A61B 3/1241* (2013.01); *A61B 3/14* (2013.01)

(58) Field of Classification Search
CPC .......... A61B 3/0025; A61B 3/14; A61B 3/12; A61B 3/113; A61B 3/102
USPC ...................................................... 351/246
See application file for complete search history.

(56) References Cited

U.S. PATENT DOCUMENTS

| | | | |
|---|---|---|---|
| 5,640,220 A | * | 6/1997 | Vo .............................. A61B 3/12 351/206 |
| 2005/0197560 A1 | | 9/2005 | Rao et al. |
| 2005/0197756 A1 | | 9/2005 | Rao et al. |
| 2010/0070249 A1 | | 3/2010 | Ionasec et al. |
| 2011/0242306 A1 | | 10/2011 | Bressler et al. |
| 2012/0236259 A1 | | 9/2012 | Abramoff et al. |
| 2015/0112182 A1 | | 4/2015 | Sharma et al. |

(Continued)

OTHER PUBLICATIONS

Kumagai, Kyoko, et al. "Three-Dimensional optical Coherence Tomography Evaluation of Vascular Changes at Arteriovenous Crossing Vascular Changes at Arteriovenous Crossings." Investigative ophthalmology & visual science 55.3 (2014): 1867-1875.

(Continued)

*Primary Examiner* — Mohammed A Hasan
(74) *Attorney, Agent, or Firm* — Cahn & Samuels, LLP

(57) ABSTRACT

An embodiment of the invention receives by an interface a retinal image from a patient, and identifies by a feature extraction device vessel fragments in the retinal image. The vessel fragments include at least a portion of a major vessel and at least a portion of a branch connected to a major vessel. A processor computes estimated blood flow velocities in the vessel fragments with a blood flow velocity estimation model and determines actual blood flow velocities in the vessel fragments. An analysis engine compares the actual blood flow velocities in the vessel fragments to the estimated blood flow velocities in the vessel fragments. The analysis engine detects a candidate plaque affected vessel fragment when the estimated blood flow velocities in the vessel fragments differs from the actual blood flow velocities in the vessel fragments by a predetermined amount.

13 Claims, 5 Drawing Sheets

(56) References Cited

U.S. PATENT DOCUMENTS

2016/0000324 A1* 1/2016 Rege ................... A61B 3/0008
351/206
2016/0270656 A1* 9/2016 Samec .................. A61B 3/085

OTHER PUBLICATIONS

Nguyen, Uyen TV, et al. "An automated method for retinal arteriovenous nicking quantification from color fundus images." IEEE Transactions on Biomedical Engineering 60.11 (2013): 3194-3203.
Roy, Pallab Kanti, et al. "A novel computer aided quantification method of focal arteriolar narrowing using colour retinal image." Computers in biology and medicine 74 (2016): 18-29.
Ganekal, Sunil. "Retinal functional imager (RFI): Non-invasive functional imaging of the retina." Nepalese Journal of Ophthalmology 5.2 (2013):250-257.

* cited by examiner

US 10,307,050 B2

EARLY PREDICTION OF HYPERTENSIVE RETINOPATHY

FIELD OF THE INVENTION

The present invention relates to systems, methods, and computer program products for early prediction of hypertensive retinopathy.

BACKGROUND

Hypertension is a serious health problem that can be associated with major complications such as coronary heart disease, stroke, chronic kidney disease, congestive heart failure, and retinopathy. Among these complications, hypertensive retinopathy can be non-invasively visualized using available retinal Colour Fundus Imaging (CFI). Hypertensive retinopathy causes gradual damage to the visual system that ultimately leads to blindness, but early detection can help clinicians to initiate preventive treatment, thereby reducing its progression. Additionally, the early prediction of hypertensive retinopathy can help to detect asymptomatic hypertensive patients who have a greater risk of stroke.

SUMMARY OF THE INVENTION

An embodiment of the invention provides a method of early detection of hypertensive retinopathy, where an interface receives retinal images of individuals in a cohort of individuals known to not have hypertensive retinopathy. A processor generates a blood flow velocity estimation model from the retinal images of the individuals in the cohort of individuals known to not have hypertensive retinopathy. The interface receives a retinal image for a patient; and, a feature extraction device identifies vessel fragments in the retinal image. The vessel fragments include at least a portion of a major vessel and at least a portion of a branch connected to a major vessel.

The processor computes estimated blood flow velocities in the vessel fragments with a blood flow velocity estimation model and determines actual blood flow velocities in the vessel fragments from a retinal functional image. An analysis engine compares the actual blood flow velocities in the vessel fragments to the estimated blood flow velocities in the vessel fragments. The analysis engine detects a candidate plaque affected vessel fragment when the estimated blood flow velocities in the vessel fragments differs from the actual blood flow velocities in the vessel fragments by a predetermined amount.

BRIEF DESCRIPTION OF THE SEVERAL VIEWS OF THE DRAWINGS

The present invention is described with reference to the accompanying drawings. In the drawings, like reference numbers indicate identical or functionally similar elements.

DETAILED DESCRIPTION

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

At least one embodiment of the invention provides a system and method for the early detection of hypertensive retinopathy via detection of vessels with a high probability of plaque, using both functional and anatomical features of the vessel. As used herein, the term "hypertensive retinopathy" includes damage to retinal circulation due to chronic high blood pressure. Anatomical features can include retinal vascular (arteriolar or venular) width, branching structure of the retinal vessel network, and/or branch angles. These features may be acquired from a retinal fundus image. Functional features can include the blood flow velocity inside each retinal vessel, which may be computed from the retinal functional images and/or multi-spectral imaging.

In at least one embodiment, the system learns a blood flow velocity estimation model of vessel branches (fragmented by the position of branch point) from a healthy cohort of retinal multi spectral images, which are used to generate the retinal functional and fundus image. Following generation of the retinal functional and fundus image, in the test phase, the system can use the blood flow model to estimate the blood flow velocity of the vessel fragments for each major vessel. The difference between the estimated velocity (computed by the blood flow model) and the actual blood flow velocity (computed from the retinal function image) of the corresponding vessel fragment can be used to detect a candidate plaque affected vessel fragment for further diagnosis.

Figure 1:
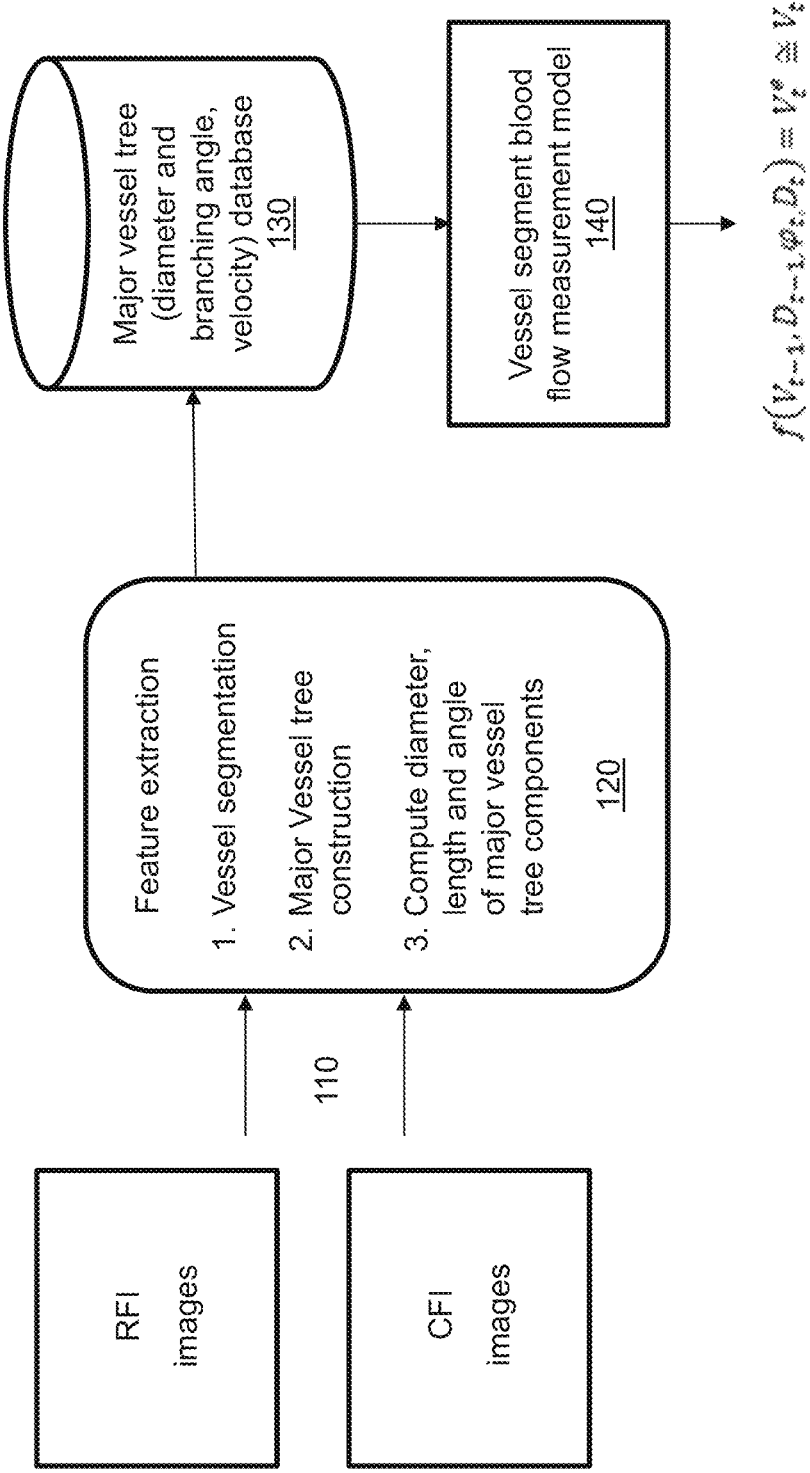
FIG. 1 is a diagram illustrating a training module according to an embodiment of the invention.
Figure 2:
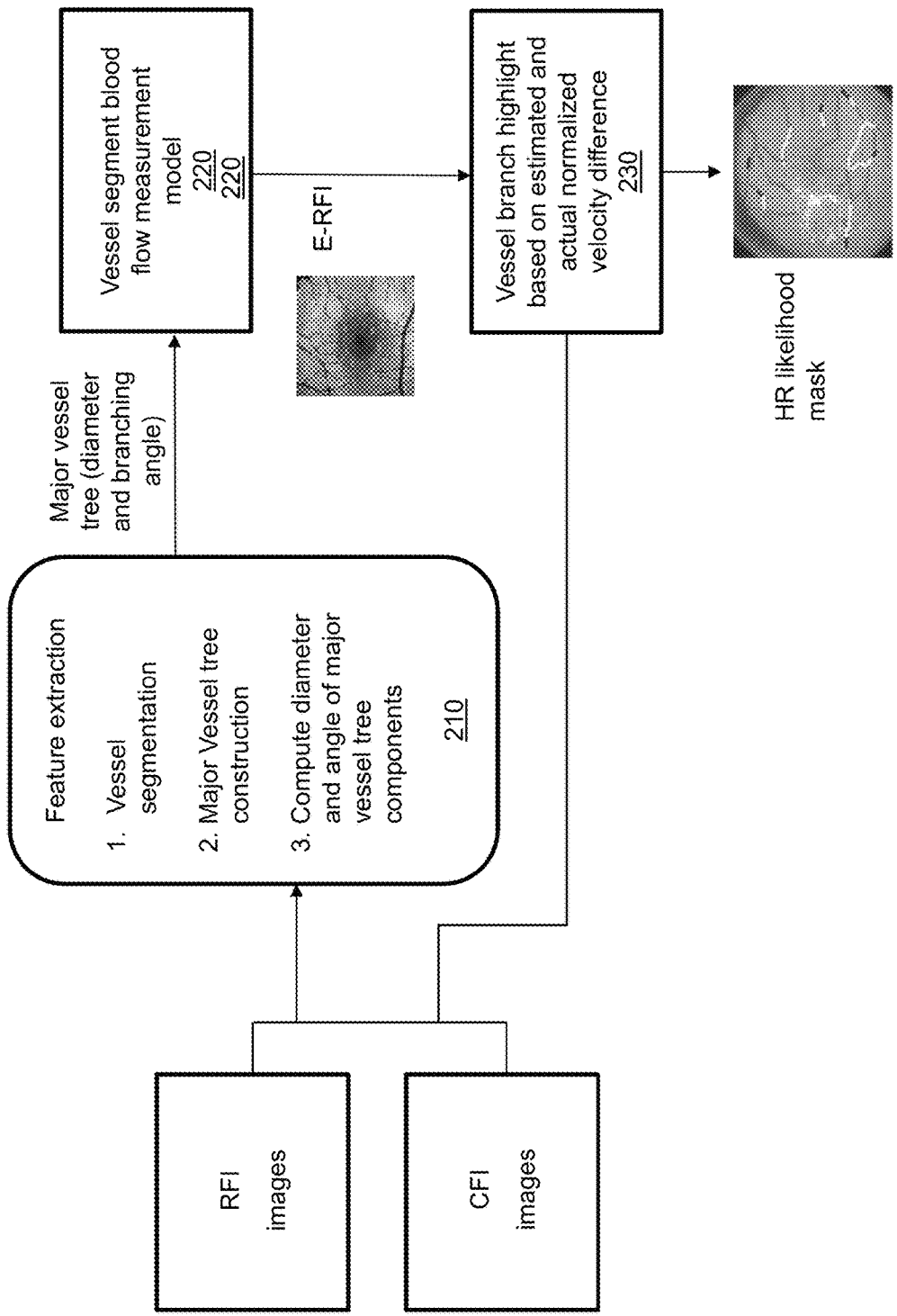
FIG. 2 is a diagram illustrating a testing module according to an embodiment of the invention.

The system and method can have two modules: training and testing as shown in FIGS. 1 and 2, respectively. The training module can have two main steps. First, the system can acquire multi-spectral and retinal fundus images of each patient as input into a feature extraction device from a cohort of healthy patients 110. For every patient, the system can identify the major vessels from the retinal colour fundus image (CFI) and traverse though the segments to construct a tree to map their branches. The system can compute the diameter, branching angle (from CFI images) and blood flow velocity (from RFI images) of the major vessels and its branches during the traversal 120. The system can create an oracle of major vessel trees and blood flow information taken from healthy patients and store the major vessel trees in a database 130. Each major vessel tree can contain the diameter, branching angle, and blood flow velocity of the parent and child branches.

In the second main step, the system can use the oracle of healthy major vessel tress to develop a model of the normal health range of blood flow in a retinal vessel's fragment 140. The system can learn a function to estimate the blood flow in vessel branch, the function can be represented as:

$$f(V_{t-1}, D_{t-1}, \varphi_t, D_t) = V_t^e \cong V_t$$

where $V_{t-1}$ and $D_{t-1}$ are the blood flow velocity and diameter of the $(t-1)_{th}$ branch, respectively, and $\varphi_t$ and $D_t$ are the branching angle and diameter of $t_{th}$ branch. This function can be represented by a Recurrent Neural Network (RNN) or Hidden Markov Model (HMM).

The test module in at least one embodiment can have three main steps. First, similar to the first training step, during the test phase, the system can construct trees of each major vessel and its branches (with diameter, branching angle, and blood velocity) for each patient 210. Then the system can re-traverse through each major vessel and use the blood flow model developed in the training phase to estimate the normal healthy blood velocity in the branches and sub-branches 220. The system can use the actual blood flow velocity (e.g., from RFI images) as the initial velocity of the major vessel for the initialization of the blood flow velocity model.

After the blood flow velocity estimation step, for each major vessel and its branches, two blood flow velocity values can be present. One value can be a measurement from RFI, and therefore an approximation of the actual velocity. The other value can be an estimate of the velocity provided by the model. The two values can be compared; and, a large difference between the estimated and actual velocity values for a particular vessel branch may be indicative of a higher probability of the vessel having plaque 230. The system can highlight those branches and refer them for further analysis using 3D optical spectral domain tomography imaging (SD-OCT).

Figure 3:
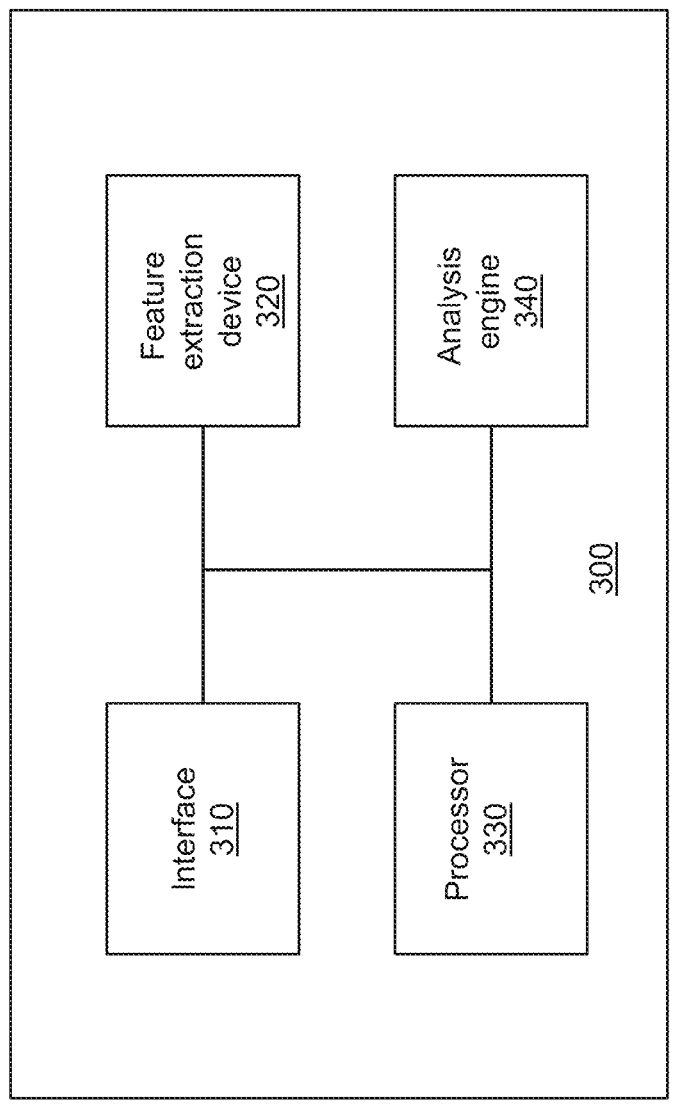
FIG. 3 is diagram illustrating a system for early prediction of hypertensive retinopathy according to another embodiment of the present invention.
Figure 4:
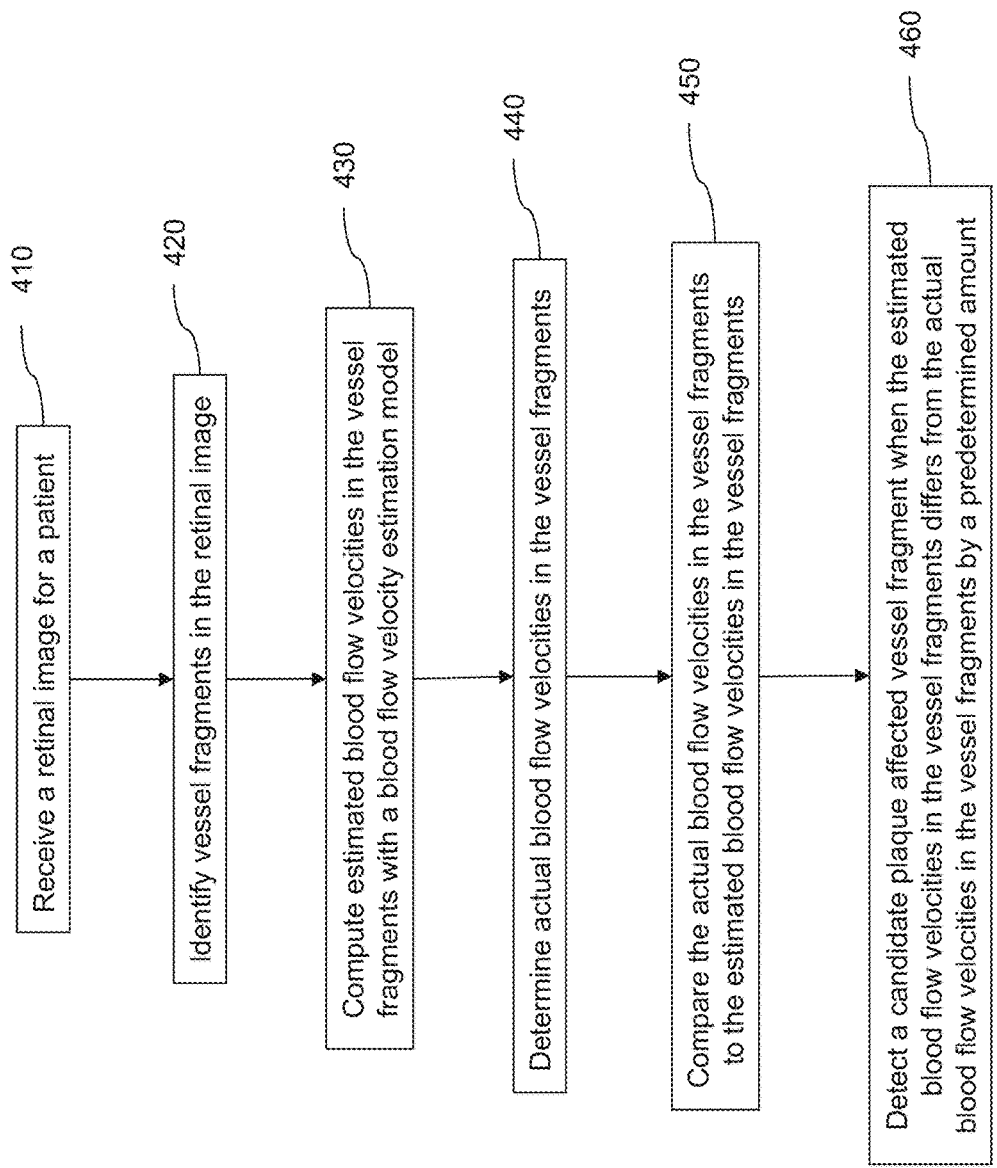
FIG. 4 is a flow diagram illustrating a method of early prediction of hypertensive retinopathy according to an embodiment of the present invention.

FIG. 3 is diagram illustrating a system 300 for early prediction of hypertensive retinopathy according to an embodiment of the present invention. FIG. 4 is a flow diagram illustrating a method of early prediction of hypertensive retinopathy (e.g., using the system 300) according to an embodiment of the present invention. The system 300 can include an interface 310 that receives a retinal image for a patient (410) and a feature extraction device 320 that identifies vessel fragments in the retinal image (420). The vessel fragments can include at least a portion of a major vessel and at least a portion of a branch connected to a major vessel. As used herein, the term "interface" includes a computer hardware device, such as, for example, a keyboard, a mouse, a microphone, a touchpad, a touchscreen, a joystick, a controller, a camera, a disk drive, an input port, an output port, an antenna, etc. As used herein, the term "feature extraction device" includes a computer hardware device connected to the interface.

In at least one embodiment of the invention, a processor 330 computes estimated blood flow velocities in the vessel fragments with a blood flow velocity estimation model (430). The blood flow velocity estimation model can include the function $f(V_{t-1}, D_{t-1}, \varphi_t, D_t) = V_t^\epsilon \approx V_t$, where $V_{t-1}$ is a blood flow velocity of a $(t-1)_{th}$ branch, $D_{t-1}$ is a diameter of the $(t-1)_{th}$ branch, $\varphi_t$ is a branching angle of a $t_{th}$ branch, and $D_t$ is a diameter of the $t_{th}$ branch. The processor 330 can also determine actual blood flow velocities in the vessel fragments (440). The actual blood flow velocities in the vessel fragments can be determined from a retinal functional image. As used herein, the term "processor" includes a computer hardware device connected to the interface and/or the feature extraction device, such as, for example, a central processing unit (CPU), an integrated circuit, or a microprocessor.

An analysis engine 340 can compare the actual blood flow velocities in the vessel fragments to the estimated blood flow velocities in the vessel fragments (450). The analysis engine 340 can detect a candidate plaque affected vessel fragment when the estimated blood flow velocities in the vessel fragments differs from the actual blood flow velocities in the vessel fragments by a predetermined amount (460). As used herein, the term "analysis engine" includes a computer hardware device connected to the processor, such as, for example, a central processing unit (CPU), an integrated circuit, or a microprocessor.

In at least one embodiment, retinal images of individuals in a cohort of individuals known to not have hypertensive retinopathy are received by the interface, where such retinal images include retinal functional images and retinal colour fundus images. Major vessels can be identified in each of the retinal colour fundus images; and, branches can be mapped from each of the major vessels to construct a tree for each of the retinal images. The processor 330 can compute a diameter of each major vessel and each of the branches from the retinal images, and a branching angle of each of the branches from the retinal colour fundus images. A blood flow velocity can be determined of each major vessel and each of the branches from the retinal functional images. The blood flow velocity estimation model can be generated from the computed diameters, branching angles, and/or blood flow velocity.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 5:
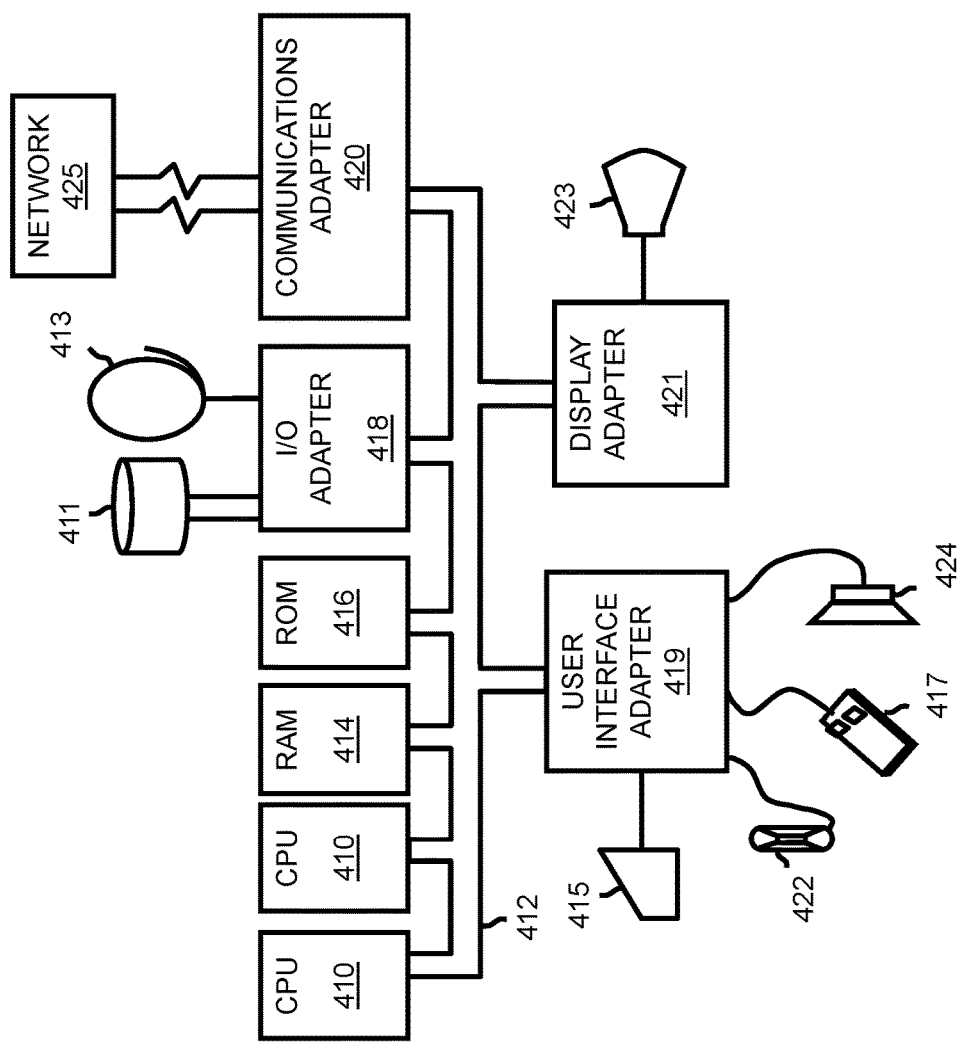
FIG. 5 is a diagram illustrating a computer program product according to an embodiment of the present invention.

Referring now to FIG. 5, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 14, or other program storage devices that are readable by the system. The system can read the inventive instructions on the program storage devices and follow these instructions to execute the methodology of at least one embodiment of the invention. The system further includes a user interface adapter 14 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 24 which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of early detection of hypertensive retinopathy, said method comprising:
    receiving by an interface a retinal image from a patient;
    identifying by a feature extraction device vessel fragments in the retinal image, the vessel fragments including at least a portion of a major vessel and at least a portion of a branch connected to a major vessel;
    computing, by processing circuitry, estimated blood flow velocities in the vessel fragments with a blood flow velocity estimation model;
    determining, via a multi-spectral imaging device and from the retinal image, actual blood flow velocities in the vessel fragments;
    comparing, by the processing circuitry, the actual blood flow velocities in the vessel fragments to the estimated blood flow velocities in the vessel fragments; and
    detecting, by the processing circuitry, a candidate plaque affected vessel fragment indicating hypertensive retinopathy when the estimated blood flow velocities in the vessel fragments differs from the actual blood flow velocities in the vessel fragments by a predetermined amount.

2. The method according to claim 1, further comprising:
    receiving retinal images of individuals in a cohort of individuals known to not have hypertensive retinopathy, the retinal images including retinal functional images and retinal colour fundus images;
    identifying major vessels in each of the retinal colour fundus images; and
    mapping branches from each of the major vessels to construct a tree for each of the retinal images.

3. The method according to claim 2, further comprising:
    computing a diameter of each major vessel and each of the branches from the retinal images; and
    computing a branching angle of each of the branches from the retinal colour fundus images.

4. The method according to claim 3, further comprising:
    determining a blood flow velocity of each major vessel and each of the branches from the retinal functional images.

5. The method according to claim 4, further comprising:
    generating the blood flow velocity estimation model from the computed diameters, branching angles, and blood flow velocity.

6. The method according to claim 1, wherein the blood flow velocity estimation model includes the function $f(V_{t-1}, D_{t-1}, \phi_t, D_t) = V_t^{dielcons_t} \approx V_t$, where $V_{t-1}$ is a blood flow velocity of a $(t-1)$th branch, $D_{t-1}$ is a diameter of the $(t-1)$th branch, $\phi_t$ is a branching angle of a $t$th branch, and $D_t$ is a diameter of the $t$th branch.

7. A method of early detection of hypertensive retinopathy, said method comprising:
    receiving, by an interface, retinal images of individuals in a cohort of individuals known to not have hypertensive retinopathy;
    generating, by processing circuitry, a blood flow velocity estimation model from the retinal images of the individuals in the cohort of individuals known to not have hypertensive retinopathy;
    receiving, by the interface, a retinal image for a patient;
    identifying, by a feature extraction device, vessel fragments in the retinal image, the vessel fragments including at least a portion of a major vessel and at least a portion of a branch connected to a major vessel;
    computing, by the processor, estimated blood flow velocities in the vessel fragments as a function of the blood flow velocity estimation model;
    determining, via a multi-spectral imaging device and based on the retinal image, actual blood flow velocities in the vessel fragments;
    comparing, by an analysis engine, the actual blood flow velocities in the vessel fragments to the estimated blood flow velocities in the vessel fragments; and
    detecting, by the analysis engine, a candidate plaque affected vessel fragment indicating hypertensive retinopathy when the estimated blood flow velocities in the vessel fragments differs from the actual blood flow velocities in the vessel fragments by a predetermined amount.

8. The method according to claim 7, wherein said receiving of the retinal images of the individuals in the cohort of individuals known to not have hypertensive retinopathy includes receiving retinal functional images and retinal colour fundus images.

9. The method according to claim 8, further comprising:
    identifying major vessels in each of the retinal colour fundus images; and mapping branches from each of the major vessels to construct a tree for each of the retinal images.

10. The method according to claim 9, further comprising:
    computing a diameter of each major vessel and each of the branches from the retinal images; and computing a branching angle of each of the branches from the retinal colour fundus images.

11. The method according to claim 10, further comprising:
    determining a blood flow velocity of each major vessel and each of the branches from the retinal functional images.

12. The method according to claim 11, further comprising:
    generating the blood flow velocity estimation model from the computed diameters, branching angles, and blood flow velocity.

13. The method according to claim 7, wherein the blood flow velocity estimation model includes the function $f(V_{t-1}, D_{t-1}, \phi_t, D_t) = V_t^{dielcons_t} \approx V_t$, where $V_{t-1}$ is a blood flow velocity of a $(t-1)$th branch, $D_{t-1}$ is a diameter of the $(t-1)$th branch, $\phi_t$ is a branching angle of a $t$th branch, and $D_t$ is a diameter of the $t$th branch.

* * * * *